(12) United States Patent
Margolis (10) Patent No.: US 7,192,438 B2
(45) Date of Patent: Mar. 20, 2007

(54) DEVICE AND METHOD FOR ELECTRICAL ISOLATION OF THE PULMONARY VEINS

(76) Inventor: James R. Margolis, 20 Tahiti Beach Island Rd., Coral Gables, FL (US) 33143

( * ) Notice: Subject to any disclaimer, the term of this patent is extended or adjusted under 35 U.S.C. 154(b) by 42 days.

(21) Appl. No.: 10/702,844

(22) Filed: Nov. 6, 2003

(65) Prior Publication Data

US 2004/0167598 A1 Aug. 26, 2004

Related U.S. Application Data

(60) Provisional application No. 60/425,142, filed on Nov. 8, 2002.

(51) Int. Cl.
*A61F 7/00* (2006.01)
(52) U.S. Cl. .................................................... 607/96
(58) Field of Classification Search ............... 128/898; 606/41, 32; 607/96, 122, 119, 101; 601/1; 604/22
See application file for complete search history.

(56) References Cited

U.S. PATENT DOCUMENTS

| | | | |
|---|---|---|---|
| 5,531,779 A | 7/1996 | Dahl et al. | |
| 5,978,705 A | 11/1999 | KenKnight et al. | |
| 6,094,596 A | 7/2000 | Morgan | |
| 6,164,283 A * | 12/2000 | Lesh | 128/898 |
| 6,266,563 B1 | 7/2001 | KenKhight et al. | |
| 6,275,730 B1 | 8/2001 | KenKhight et al. | |
| 6,397,109 B1 | 5/2002 | Cammilli et al. | |
| 6,500,174 B1 * | 12/2002 | Maguire et al. | 606/41 |
| 6,632,223 B1 * | 10/2003 | Keane | 606/41 |
| 6,716,242 B1 * | 4/2004 | Altman | 623/1.42 |
| 2003/0018362 A1 | 1/2003 | Fellows et al. | |
| 2003/0055491 A1 | 3/2003 | Schwartz et al. | |
| 2003/0069606 A1 | 4/2003 | Girouard et al. | |

FOREIGN PATENT DOCUMENTS

WO WO 03/003948 1/2003

OTHER PUBLICATIONS

Vance et al; "Successful Stent Treatment of Pulmonary Vein Stenosis Following Atrial Fibrillation Radio Frequency Ablation"; Journal of Invasive Cardiology; vol. 14, No. 7; pp. 414-416; Jul. 2002.
Saad et al; "Ablation of Focal Atrial Fibrillation"; Cardio Electrophysiology Review; vol. 6, No. 4; pp. 389-396; Dec. 2002.

* cited by examiner

*Primary Examiner*—Kevin T. Truong
(74) *Attorney, Agent, or Firm*—Nixon & Vanderhye PC (57) ABSTRACT

A method and device for the treatment of atrial fibrillation by inhibiting the flow of electricity from the pulmonary vein to the left atrium. The method includes inhibiting electrical flow by disabling the conductive fibers mechanically, using an incision (70), or via fibrosis, or chemically by applying toxic substances to the fibers. In one embodiment, a device (30) is useable to deliver a prosthetic structure (10) to the pulmonary vein that is useable to stretch the pulmonary vein, thereby inducing fibrosis, keeping the incision (70) open, or delivering a substance to the endothelium of the pulmonary vein. The structure (10) delivered by the device (30) is a self-expanding prosthetic structure. In another embodiment, a device (60) is useable to deliver and expand a prosthetic structure (10) that is expandable but not self-expanding.

14 Claims, 6 Drawing Sheets

DEVICE AND METHOD FOR ELECTRICAL ISOLATION OF THE PULMONARY VEINS

CROSS REFERENCE TO RELATED APPLICATIONS

This application claims priority from provisional patent application Ser. No. 60/425,142, filed Nov. 8, 2002.

BACKGROUND OF THE INVENTION

This invention relates generally to methods and devices used to treat arrhythmias. In particular, this invention relates to treatment of paroxysmal atrial fibrillation by electrical isolation of the pulmonary veins from the left atrium of the heart.

Atrial fibrillation is the most common form of cardiac arrhythmia and affects approximately 1.5 million patients in the United States annually, causing considerable morbidity as well as mortality. Additionally, atrial fibrillation is the leading cause of embolic stroke, leading to over 70,000 cerebrovascular failures per year.

There is extensive literature documenting the role of the pulmonary veins as the origin of excitatory impulses in patients with paroxysmal atrial fibrillation. There is a 70% cure rate in the treatment of paroxysmal atrial fibrillation and a 30% cure rate in the treatment of fixed atrial fibrillation when the pulmonary veins are electrically isolated.

Physicians may employ a variety of methods for treating patients with atrial fibrillation, including drug therapy, surgery and catheter ablation. Most patients prefer drug therapy because it is the most non-invasive treatment. However, drug therapy typically treats the symptoms of atrial fibrillation rather than the cause.

Several surgical techniques have been developed for the treatment of atrial fibrillation. These, techniques include implanting defibrillators or pacemakers or utilizing one of a variety of open-heart or percutaneous procedures to modify or inhibit cardio-electric impulses leading the atrial fibrillation. U.S. Pat. Nos. 5,531,779, 5,978,705, 6,094,596, and 6,275,730 disclose different surgical techniques in which defibrillators or pacemakers are implanted in the body to stimulate the heart in manner that prevents irregular rhythms. These implanted devices stimulate the heart at a slightly higher than normal rate in an effort to control the heart rate and avoid atrial fibrillation. However, implanting such devices requires invasive surgery and monitoring for post-implant complications.

The most common surgical procedure in the treatment of atrial fibrillation is the Maze procedure, originally developed by Dr. James L. Cox. When performing this procedure, first an electrophysiology study is conducted to map the electrical impulses and conduction pathways in the cardiac chambers and to determine the cardiac tissue that is causing the arrhythmia. Next, an open-heart or percutaneous procedure is used to make one or more controlled incisions in the wall of the left atrium running from the right and left superior pulmonary vein, following along both inferior pulmonary veins, and terminating at the annulus of the mitral valve. An additional incision is made connecting the superior ends of the first incisions, effectively isolating the pulmonary vein ostia from the remaining atria tissue by creating conductive blocks. While surgical techniques, such as the Maze technique, have proven successful is treating atrial fibrillation, they are highly invasive, generate a host of post-operative complications, require lengthy patient recovery times and are costly.

Thermal ablation techniques, such as radio frequency (RF) ablation and microwave ablation, have also been successful in treating atrial fibrillation. Thermal ablation typically involves the use of a catheter having one or more electrodes at or near its distal end. Once the catheter has been properly positioned in the atrium, the device is energized so as to evaporate water contained in the target tissue rendering it non-conductive. While thermal ablation has been successful in treating atrial arrhythmias, there are several problems associated with it. Microwave generators necessary for microwave ablation techniques tend to be prohibitively expensive for most catheter laboratories. RF generators produce electrical "noise" that interferes with the physician's ability to use electrocardiographic and other patient monitoring equipment during the ablation procedure. The catheters used in both types of thermal ablation tend to create coagulum at the distal tip, creating higher instances of cerebrovascular events due to the dislodged coagulum. Thermal ablation techniques also require meticulous tracking of electrical impulses with a second transeptally placed catheter. This is excessively time consuming. Finally, extensive ablation within the pulmonary veins themselves has led to pulmonary venous stenosis and pulmonary hypertension. To prevent the devastating effects of stenosis in all four pulmonary veins, thermal ablation is usually performed as two or more partial procedures, with a recovery period between surgeries, adding significant costs, patient time, and discomfort.

U.S. Pat. Nos. 6,266,563 and 6,397,109, U.S. patent application Nos. US 2003/0055491 (WO 03/003948), US 2003/0018362, and US 2003/0069606, and Bernstein et. al, Successful Stent Treatment of Pulmonary Vein Stenosis Following Atrial Fibrillation Rediofrequency Ablation, THE JOURNAL OF INVASIVE CARDIOLOGY, Jul. 2002, at 414, disclose various stenting techniques which attempt to address the problems associated with ablation procedures. Stenting has historically been used in interventional procedures as a means of maintaining the patency of a diseased conduit in the body. Stents are typically expandable tubular structures comprised of metals, metal alloys, composites, or polymers that are navigated through a conduit in the body, while secured to the distal end of a deployment catheter. Stents can be self expanding, or deployed with the aid of a balloon or other mechanical device. Stenting has been employed in several areas of the human body including peripheral and coronary arteries and veins, both biliary and bronchial trees, as well as in the ureters and fallopian tubes, for the sole purpose of maintaining the conduit's patency. While the combination of stenting either after or during the ablation process has been successful in treating atrial fibrillation, serious problems associated with the burning and scarring of the ablated tissue persist. The most common problem associated with stricture of the pulmonary vein after stenting and ablation is the backing up of blood in the lungs.

Despite the advances made in the treatment of atrial fibrillation, there continues to be a need for a non-invasive, inexpensive technique to prevent atrial fibrillation without creating post-operative or post-procedure complications. More importantly, there is the need for a preventative alternative to thermal ablation techniques to avoid pulmonary vein stenosis.

BRIEF SUMMARY OF THE INVENTION

The present invention meets the aforementioned needs by providing a method and device for treating and/or preventing atrial fibrillation by electrically isolating the pulmonary vein from the left atrium. More specifically, electrical isolation is achieved by severing the conductive fibers found just below the surface of the endothelial layer of the pulmonary vein. After the fibers are severed, measures are taken to ensure conductivity is not reestablished.

In one aspect of the invention, a circumferential incision is made within the pulmonary vein. Circumferential incisions are preferable to ensure that complete severance of essentially all of the conductive fibers is achieved. Additionally a circumferential incision can be accomplished with minimal trauma, distinguishing this procedure from the Maze procedure, described above, which requires several longitudinal cuts to be made inside the left atrium. These long incisions require significant surgical skill, not only to effect the incisions in the optimal locations, but also to make the incisions at a desired depth and ensure the incisions intersect adequately. Recovery time for this invasive procedure is necessarily lengthy. A circumferential incision can be performed with a device, such as a cutting balloon, that makes a controlled, circular cut, having a predetermined depth, and leaves little room for error. A surgeon is tasked only with locating the cutting balloon in the desired location and inflating the balloon to a desired pressure.

In another aspect of the invention, a circumferential incision is made using a catheter-carried implement, such as a rotatable knife, or an implantable structure such as a stent or a ring.

In another aspect of the invention, the incision, once made by any appropriate means, is prevented from healing in a manner that conductivity may be reestablished. One preferred measure is to apply a toxin to the incision, thereby killing the termini of the fibers in the incision. Another preferred measure is to keep the incision open, either while the incision is healing, or permanently, using an expandable stent, ring, or other structure. Yet another preferred measure is to apply a skin-forming compound to the open incision after it is made, to prevent the termini from re-contacting each other during the healing process.

Delivery of the aforementioned structures and treatments may be accomplished using accepted procedures and devices. By way of example, in some instances a structure and delivery system would be introduced through a guiding catheter that has been placed in the patient's femoral vein as part of a typical interventional procedure and navigated to the pulmonary veins over a guide wire via a transeptal puncture. Alternatively, the system might be introduced retrograde across the aortic and mitral valves.

In other instances it may be necessary to introduce a structure and delivery system through an "open chest" (thoracotomy) procedure, or the less invasive "port access" method, both, typically used in open heart procedures, depending on the needs of a particular device or clinical situation.

In one aspect of the present invention, the structure delivered is a self expanding stent fabricated out of a tube or flat sheet, the tube or flat sheet being made from a shape memory alloy such as Nitinolâ, Nitinol, or a cobalt/platinum based alloy. Shape memory alloys (SMA) have long been used in medical devices because of their ability to be processed and "shape set" into a desired final configuration and then manipulated into a low profile configuration that may be more easily navigated through a tortuous location in the body, such as a coronary artery or pulmonary vein. This shape setting is typically achieved by heating the SMA above a certain temperature known as the "transition temperature," which causes any deformation introduced below the transition temperature to be reversed. Additionally, the use of stress-induced martensite alloys decreases the temperature sensitivity of the devices, making them easier to navigate and deploy. The use of these alloys as described, are discussed in detail in U.S. Pat. No. 4,485,816 (Krumme), U.S Pat. Nos. 4,665,906 and 6,306,141 (Jervis), each of which are incorporated herein by reference.

Alternatively, the structure deployed may be a self-expanding stent fabricated out of a tube or flat sheet, the tube or flat sheet being made from a shape memory polymer (SMP). Shape memory polymers are to be considered as these polymers can be shape-set in seconds at comparatively low temperatures, and can withstand deformations of several hundred percent. Additionally, SMP's are typically non-conductive in nature.

The deployed structures, rather than being self-expanding, may be expandable with an expansion device such as a balloon or similar mechanism. For example, an expandable stent fabricated out of a tube or flat sheet, the tube or flat sheet being made from a binary alloy such as tantalum-tungsten or tantalum-niobium, may be deployed and mechanically expanded.

As stated above, many acceptable materials and devices may be employed as delivered structures to the site of desired reduced electrical conductivity. More examples of acceptable devices and materials include, but are not limited to: binary alloys having enhanced radiopacity, such as are discussed in detail in WO 02/05863 (Pacetti et al), incorporated herein by reference; stents fabricated out of a tube or flat sheet, the tube or flat sheet being made from 316 L or any other acceptable stainless steel, and deployed with the aid of a balloon or similar mechanical device; stents manufactured using any accepted techniques such as etching, laser cutting, or braiding; self-expanding, or balloon-expandable rings designed to cover the pulmonary vein ostium; coated stents, covered stents, drug-eluting stents, and the like.

A preferred embodiment of a coated or covered stent uses cyanoacrylate and/or other biocompatible adhesives that are commercially available for adhering a non-conductive fabric to a metal, metal alloy, composite, or polymer expandable structure, for the purpose of electrically isolating that structure from the pulmonary veins.

Another embodiment of a coated or covered structure includes a structure that is coated with a hydrophilic thrombus inhibiting polymeric agent such as Heparin, or Heparin-benzalkonium cloride.

Yet another embodiment of a coated structure for use in the present invention is one that is coated with an anti-proliferative agent including but not limited to Paclitaxel, Rapamycin, discodermolide, or ecteinascidin 743 to help combat in-stent restenosis.

Another aspect of the present invention employs an expandable stent or ring that has been made radioactive using a low level beta, or gamma, or a combination of one or more isotopes with a relatively short "half-life". These isotopes would include, but should not be limited to, Phosphorus 32, Iridium 192, Yttrium 90, Palladium 103, or Strontium 90, to name just a few. Stents and other devices can be made radioactive through various commercially available processes such as "ion implantation" or applied coating to name just two. Forschungszentrum Karlsruhe, GmbH in Karlsruhe, Germany; or MDS Nordion, in Kanata, Ontario, Canada are just two of the commercial facilities able to provide ion implantation services.

In addition, or as alternative to, making an incision and keeping it open, there is convincing data that trauma to tissue, and subsequent fibrosis or restenosis, results in significantly reduced tissue conductivity. Thus, encouraging fibrosis or restenosis, without jeopardizing the patency and flow capacity of the pulmonary vein, could result in effective electrical isolation of the left atrium from the pulmonary vein.

Numerous data exist that correlate in-stent restenosis with the percentage of stent to tissue contact. As such, currently marketed coronary stents, will typically have 20% material contact with the tissue layers of the vessel, once deployed. Increasing the percentage of stent to tissue contact may increase the likelihood that the aberrant conductive pathway creating the arrhythmia is cut when a stent is deployed, in one or more of the pulmonary veins, or it's surrounding tissues and structures.

Another aspect of the present invention provides a means for monitoring the effectiveness of the procedure. For example, a preferred embodiment provides a detachable wire fixedly attached to the distal end, and proximal end of the stent or ring structure so that the user can measure electrical continuity between the distal and proximal ends of the non-conductive structure once it has been deployed in the pulmonary vein, or it's surrounding tissues and structures. Non-conductivity may be an inherent property of the material used to create the structure. Alternatively, the inner and outer surface of the expandable structure may be treated or coated with a non-conductive coating so as to disrupt the aberrant conductive pathway, and to allow the employment of monitoring wires on either end of the structure, so as to accurately monitor current flow through the tissue rather than through the structure itself.

It is finally contemplated that the methods and devices of the present invention may be used to combat neuroconductive disorders such as epilepsy, as an example, by applying the structures and techniques to one or more of the vessels and/or tissues in the brain.

DETAILED DESCRIPTION OF THE INVENTION

Figure 1:
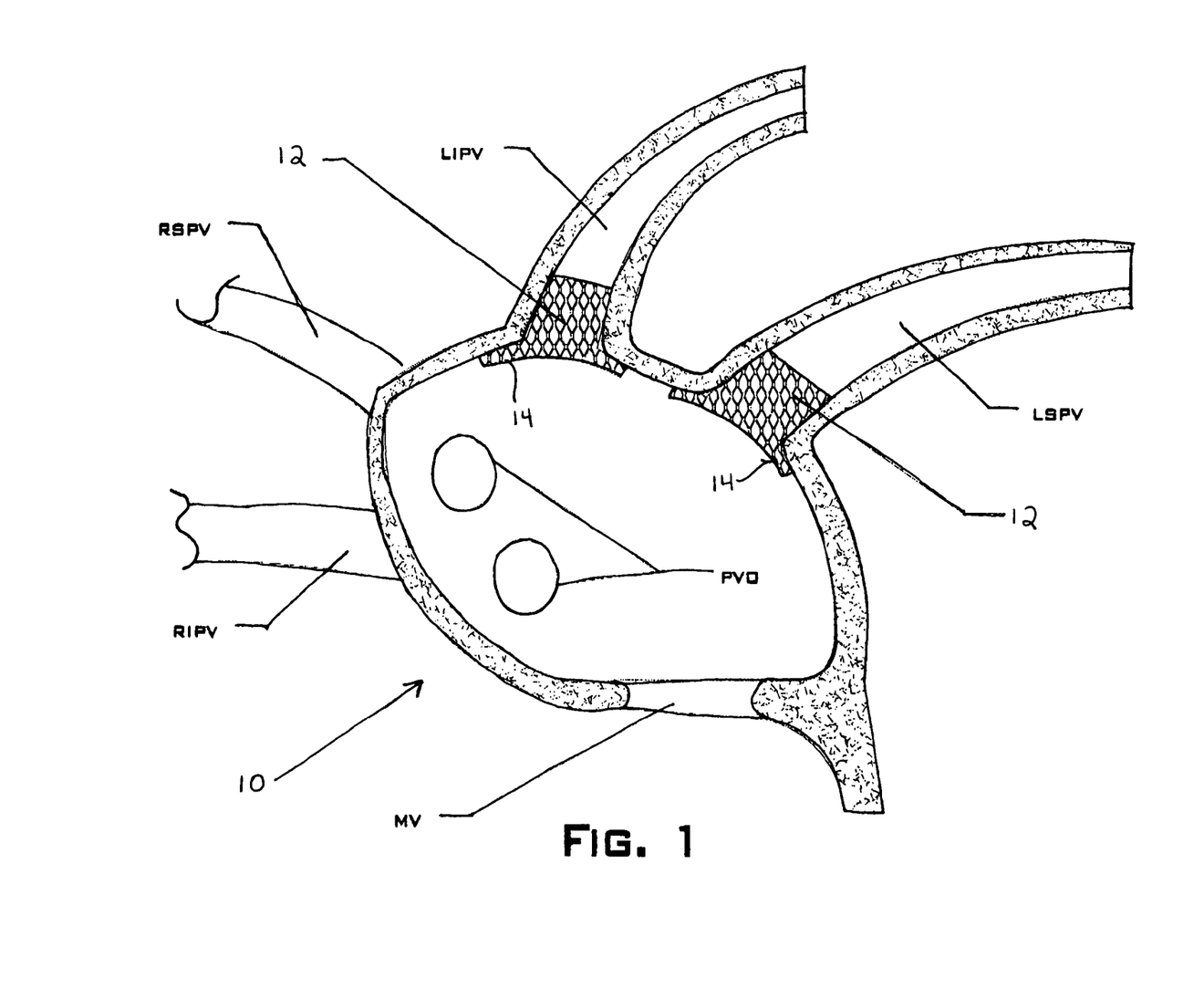
FIG. 1 is a sectional view of a preferred embodiment of the present invention.

FIG. 1 shows a preferred use of an embodiment of a structure 10 of the present invention. The structure 10 in this embodiment is a stent 12 deployed in both the left inferior pulmonary vein (LIPV) and the left superior pulmonary vein (LSPV). The stent 12 includes a flared end 14 that is constructed and arranged to extend past the ostium of the the pulmonary vein and into the left atrium (LA).

The stent 12 is preferably constructed and arranged to maintain an outward force on the endothelium of the pulmonary vein and the left atrium, thus keeping the stent 12 in place and operating to prevent electrical communication between the pulmonary vein and the left atrium. The outward force is obtained through the use of an expandable stent, such as a self-expanding or mechanically expanding stent. The outward force necessary is dependent on the principal being practiced to prevent the electrical communication between the pulmonary vein and the left atrium.

For example, one method of the present invention for preventing the aforesaid electrical flow is to stretch the endothelium, thereby inducing electrically-resistive fibrosis to occur. In this embodiment, the outward force exerted on the pulmonary vein by the stent 12 holds the pulmonary vein in a stretched condition sufficient to induce fibrosis.

Another method of the present invention for preventing the aforesaid electrical flow is to cut the current-carrying fibers in the endothelium and then stretching the pulmonary vein sufficiently to prevent the newly created fiber termini from reestablishing contact with each other. It is envisioned that the outward force necessary to keep the incision open would be less than that necessary to maintain the pulmonary vein in a stretched state.

If the stent 12 is to include a flared end 14, the desired shape can be established prior to compressing the stent into a delivery device (not shown in FIG. 1 but discussed below). Using a flexible bio-compatible material allows the stent to be compressed and released without significantly changing the configuration of the stent 12. Acceptable examples of bio-compatible materials include, but are not limited to, stainless steel, shape memory alloy, shape memory polymers, and stress-induced martensite alloys. Elasticity and flexibility can be enhanced using various stent construction variations such as braiding density or fenestrated stent designs. Some of the currently marketed self-expanding stents 101 include, but are not be limited to, the Schneider Wallstent, the SciMED RADIUSÔ, the Medtronic Cardiocoil, the Johnson & Johnson S.M.A.R.TÔ Stent, and Guidant's DYNALINKÔ.

Figure 2:
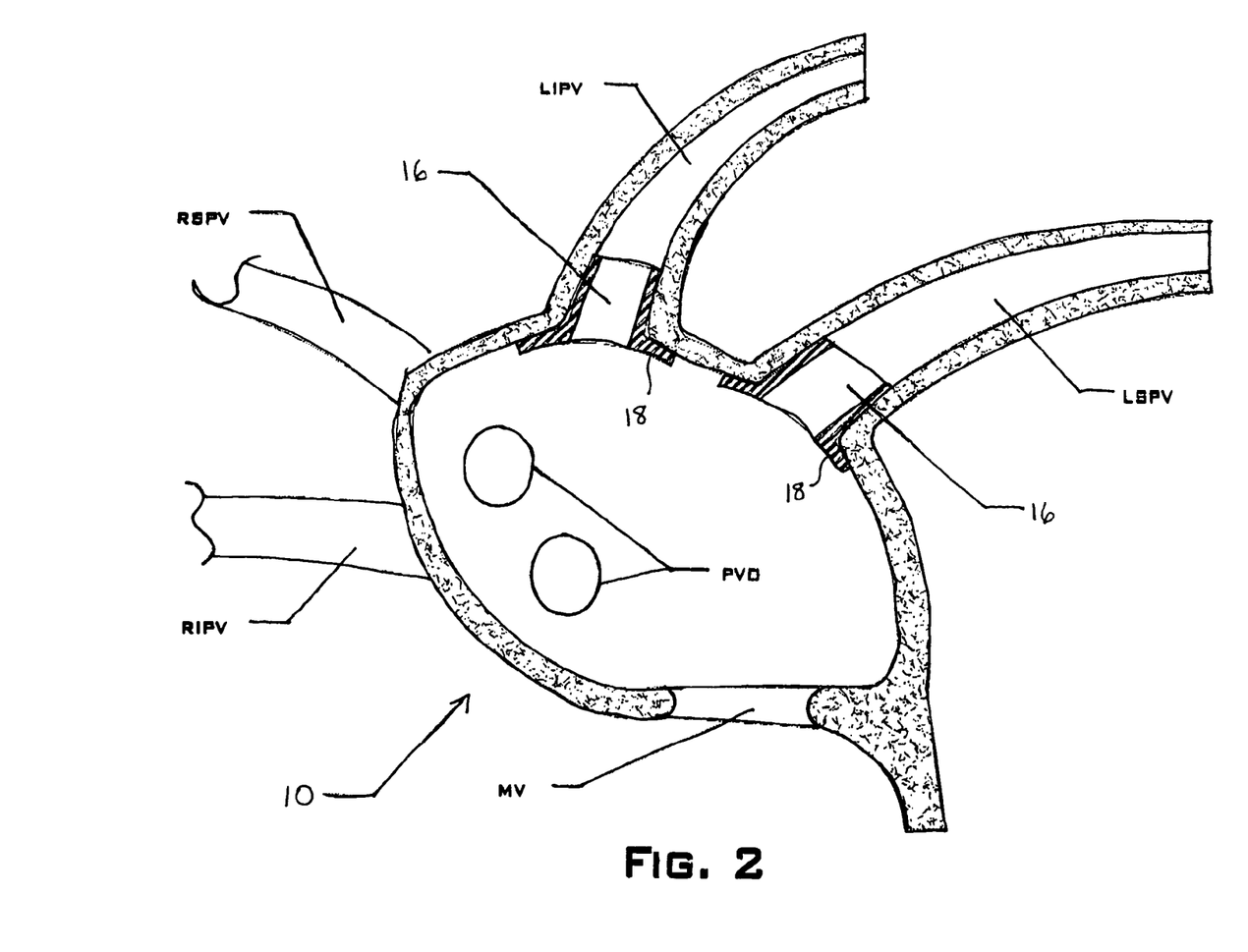
FIG. 2 is a sectional view of an alternative preferred embodiment of the present invention.

It is understood that the structure 10 of the present invention is not limited to stents 12. Referring now to FIG. 2, there is a shown a preferred use of an embodiment of a structure 10 whereby the structure 10 is a ring 16 deployed in both the left inferior pulmonary vein (LIPV) and the left superior pulmonary vein (LSPV). The ring 16 may also include a flared end 18 that is constructed and arranged to extend past the ostium of the the pulmonary vein and into the left atrium (LA).

Construction and material considerations for the ring 16 are essentially the same as those considerations for the stent 12 mentioned above. A ring 16 may be preferable to a stent 12 in applications whereby it is desired to maximize the contact area between the endothelium of the pulmonary vein and the structure 10.

The electrical inhibiting effects of placing the structure 10 in the pulmonary vein may be enhanced chemically through the use of various coatings and/or coverings. Coatings are herein distinguished from coverings as being non-fibrous chemically bonded materials bonded to the surfaces of the individual elements of the structure 10. Coatings are typically applied via electroplating, dipping or spraying. Coverings are typically fabric-like fibrous materials that span any individual interstices of the structure 10. Coverings may be woven, electro-spun, pressed or sprayed. Coverings typically cover only the exterior surfaces of the structure 10 whereas coatings may completely encompass all surfaces of the structure 10, being applied as sparsely or generously as needed to accomplish the desired result. Coatings and coverings will be collectively referred to herein as layers.

Figure 3:
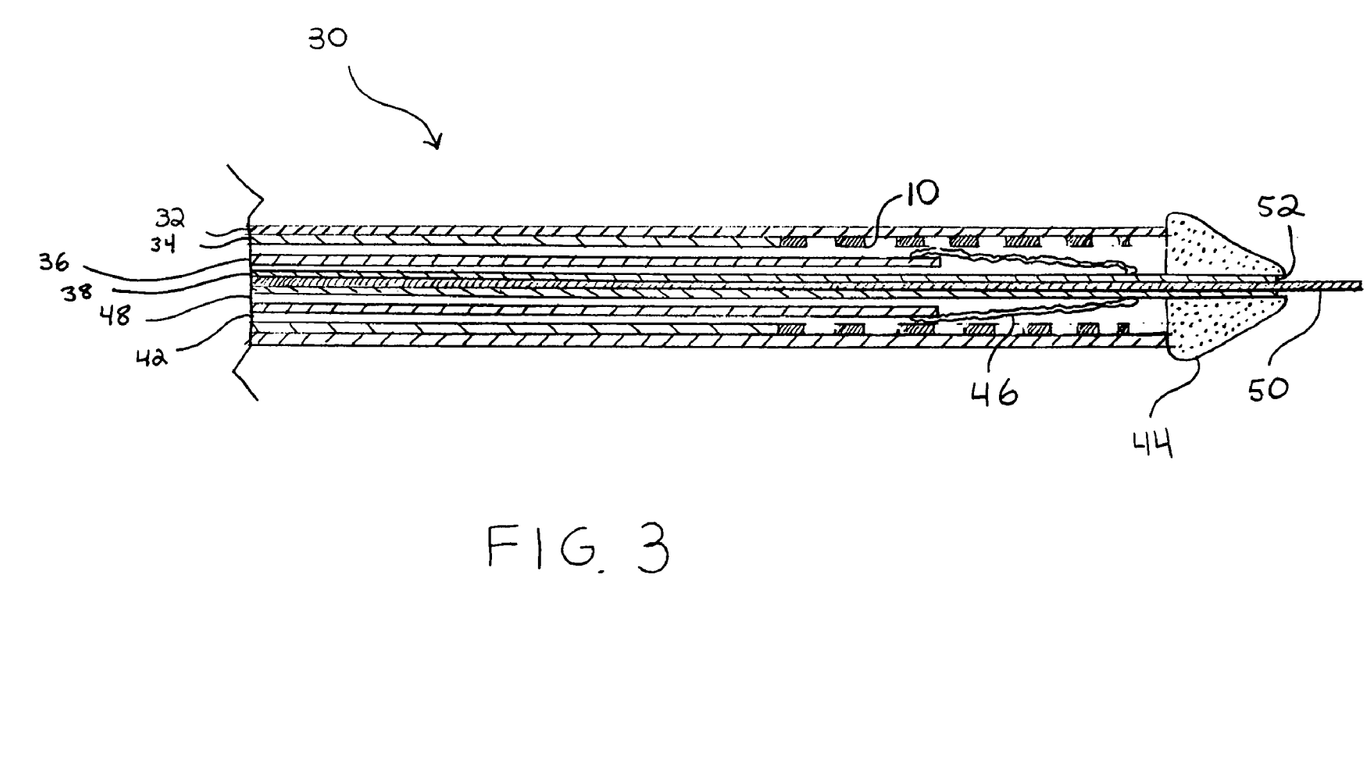
FIG. 3 is a sectional view of a preferred delivery device of the present invention.

Layers envisioned for use with the structures 10 and methods of the present invention include, but are not limited to: conductive layers useable to short-out the natural conductive pathways; non-conductive layers useable to block the natural conductive pathways; a layer that includes a hydrophilic thrombus inhibiting polymeric agent such as Heparin or Heparin-benzalkonium chloride; a layer of an anti-proliferative agent including but not limited to Paclitaxel, Rapamycin, discodermolide, or ecteinascidin 743 to help combat in-stent restenosis; a layer made radioactive using a low level beta, and, or, gamma isotope such as but not limited to, 32-phosphoris or 192-iridium Yttrium 90, Palladium 103, or Strontium 90, to name a few;

Referring now to FIG. 3, there is shown a preferred deployment device 30 of the present invention for use in deploying a self-expanding structure 10. The deployment device 30 is a catheter assembly including a plurality of concentric elongate tubes of varying diameters. These elongate tubes include, from an exterior of the device 30 to an interior, a retractable sheath 32, a stop 34, an exterior balloon catheter 36, and an interior balloon catheter 38.

The retractable sheath 32 is sliding disposed around the stop 34. The stop 34 has an outer diameter that is slightly smaller than an interior diameter of the retractable sheath 32, thereby allowing the two components to slide relative to each other. The stop 34 is shorter than the overall length of the device 30, allowing room distal of the stop 34 for a self-expanding structure 10. The retractable sheath 32 functions to prevent the self-expanding structure 10 from expanding until the sheath 32 is retracted. The stop 34 functions to act against the self-expanding structure 10 to prevent the structure 10 from retracting with the sheath 32.

The stop 34 includes a lumen 42 that contains the exterior and interior balloon catheters 36 and 38. The interior balloon catheter 38 fits within a lumen of the exterior balloon catheter 36. The interior balloon catheter 38 is longer than the exterior balloon catheter 36 and extends distally farther than any of the other aforementioned elongate tubes 32, 34, and 36. Around a distal end of the interior balloon catheter 38 there is disposed an atraumatic tip 44. The additional length of the interior balloon catheter 38 provides adequate support for the soft atraumatic tip 44.

Proximal of the atraumatic tip 44, a distal end of a tapered balloon 46 is attached to the exterior surface of the interior balloon catheter 38. A proximal end of the tapered balloon 46 is attached to the distal end of the exterior balloon catheter 36. A significant difference in the interior diameter of the exterior balloon catheter 36 and the outer diameter of the interior balloon catheter 38 creates a gap 48 therebetween. The gap 48 is in fluid communication with the interior of the tapered balloon 46 and is thus used to send a bio-compatible fluid, such as saline, to and from the tapered balloon 46 for purposes of inflating and deflating the balloon 46, respectively. Also, the interior balloon catheter 38 optionally includes a lumen through which a guidewire 50 is slidingly disposed.

In operation, the guidewire 50 may be used in conjunction with a steerable catheter (not shown) to place a distal end of the guide wire past the desired target location where the structure 10 is to be placed, such as in the pulmonary vein. Once in place, the steerable catheter is retracted off of the guidewire 50, leaving the guidewire 50 in place. The guidewire 50 is then used to locate the delivery device 30 at the desired location.

The distal end 52 of the interior balloon catheter 38 is threaded over a proximal end of the guidewire 50, and the device 30 is slowly advanced down the guidewire 50 while maintaining a stationary relationship between the guidewire 50 and the patient. While the device 30 is being advanced, the atraumatic tip 44 serves to guide the device 30 into the centers of the various body lumens en route to the desired destination as well as preventing the device 30 from causing any soft tissue damage. Notably, the atraumatic tip 44 has a narrow distal end 54 and a wider proximal end 56. Preferably, the wider proximal end 56 has a greater diameter than the diameter of the sheath 32, to prevent the relatively squared distal end of the sheath 32 from causing any damage.

Once the atraumatic tip 44 has reached the desired location where the structure 10 is to be deployed, the tip 44, as well as the interior and exterior balloon catheters 38 and 36 are advanced farther until the balloon 46 extends past the distal end of the retractable sheath 32 and past the distal end of the structure 10.

Next, the balloon 46 is inflated by pumping fluid from the proximal end of the device 30, through the gap 48, and into the balloon 46. Inflating the balloon 46 not only centers the device 30 in the pulmonary vein, but it also pre-stretches the pulmonary vein, thereby allowing the self-expanding structure 10 to expand to a greater size than if the structure 10 were expanding against the resistive force of the pulmonary vein. Most self-expanding structures are more capable of resisting collapse than they are capable of expanding against counteracting forces.

Figure 4:
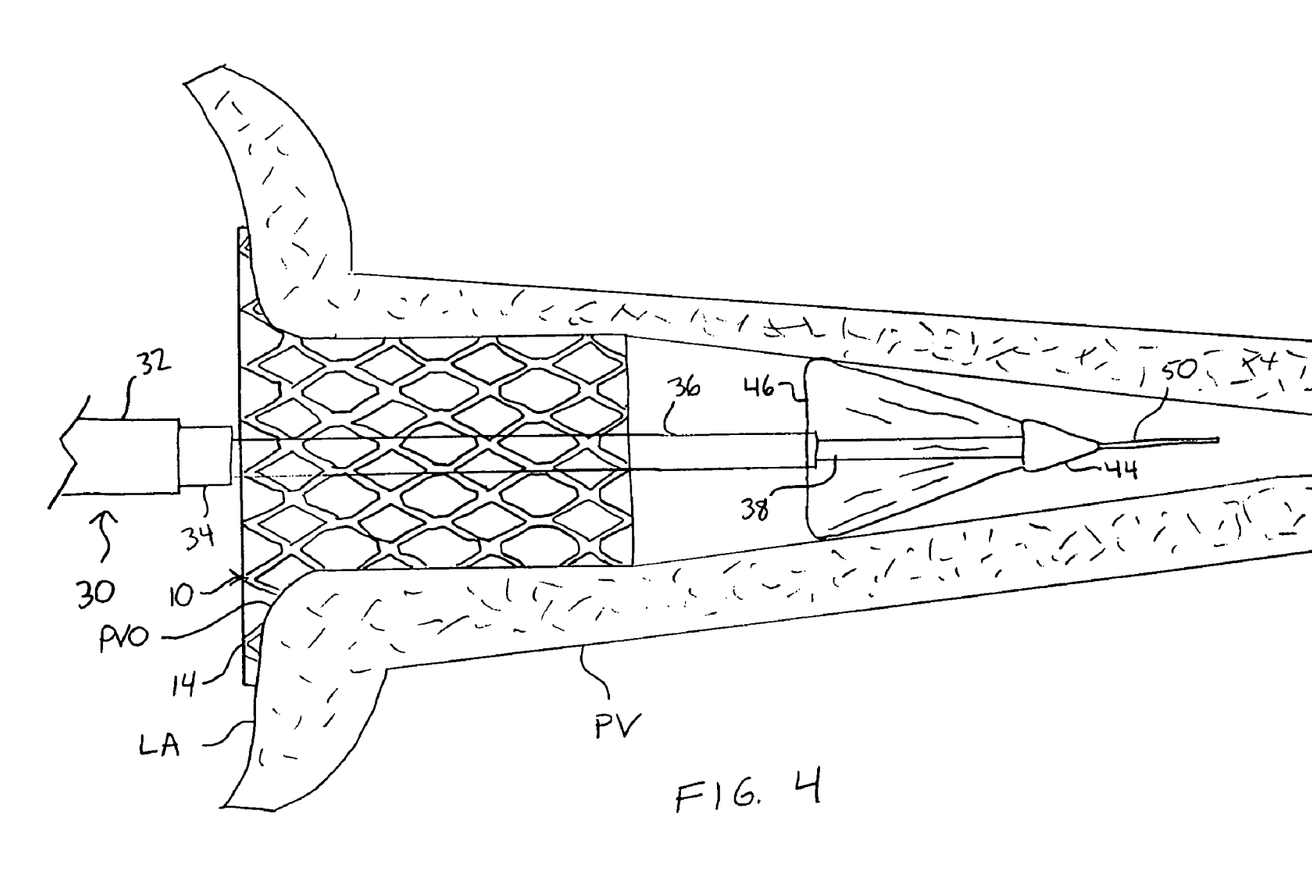
FIG. 4 is a sectional view of the delivery device of FIG. 3 in an extended state.

Once the balloon 46 is inflated, the sheath 32 is retracted until the self-expanding structure 10 is completely exposed. The self-expanding structure 10 immediately deploys, expanding to at least the size of the interior of the pulmonary vein. FIG. 4 shows a device 30 that has been used to deploy a self-expanding structure 10. A preferred shape of the tapered balloon 46 is shown. The sheath 32 has been retracted past the stop 34, allowing the structure 10 to expand. The structure 10 has a flared end 14 that hugs the interior wall of the left atrium LA, thereby allowing the structure 10 to completely cover the ostium of the pulmonary vein PVO.

Figure 5:
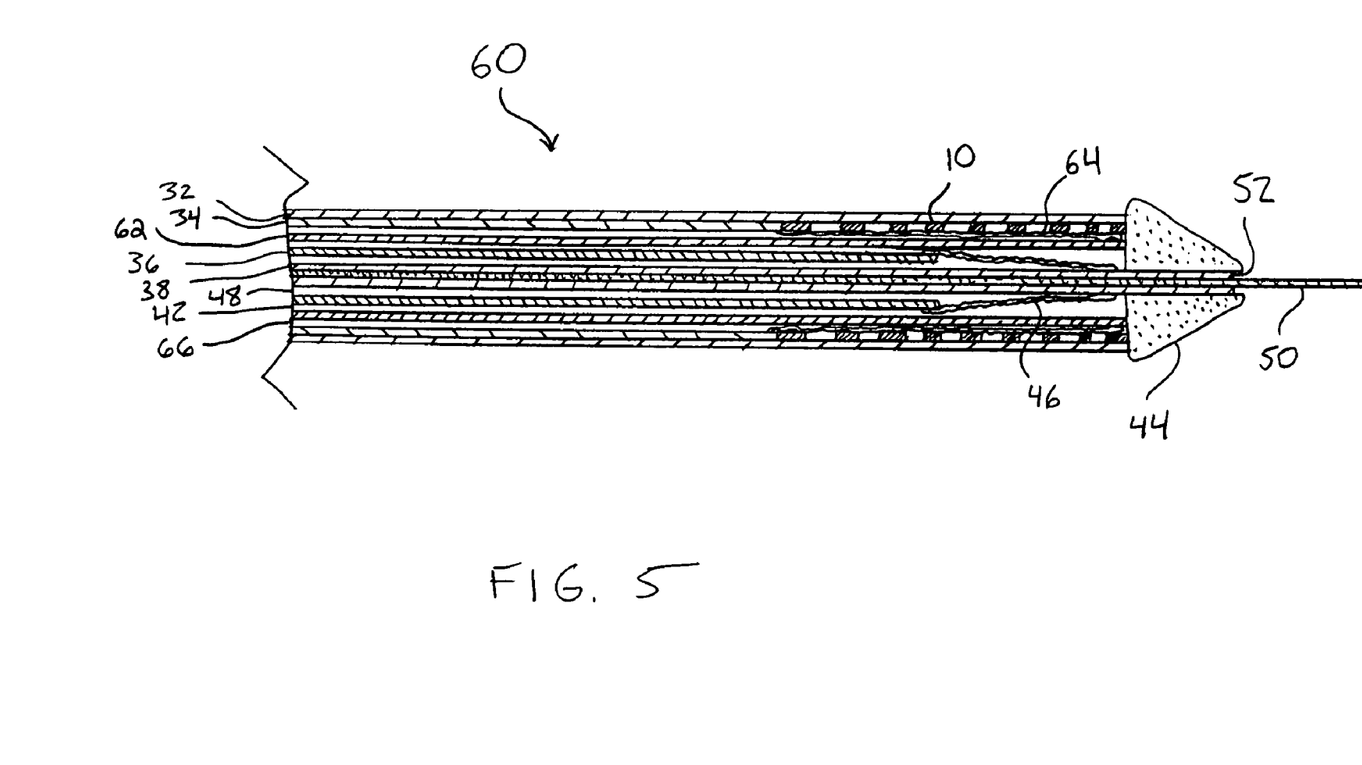
FIG. 5 is a sectional view of a second preferred delivery device of the present invention; and, FIG. 6 is a sectional view of the delivery device of FIG. 5 in an extended state.

FIG. 5 shows a device 60 of the present invention that is useable with a structure 10 that is balloon-expandable. The structure 10 may be a balloon expandable stent. Some of the currently marketed balloon expandable stents 109 include, but are not be limited to, the Johnson & Johnson Bx VELOCITYâ and entire Palmaz-SchatzÔ line of stents; Guidant's MULTILINKÔ and subsequent generations, Medtronic's AVE Micro Stent and subsequent generations, and Boston Scientific's NIR and Express stents to name just a few. The device 60 also includes a plurality of concentric elongate tubes of varying diameters. Like the device 30, these elongate tubes include, from an exterior of the device 30 to an interior, a retractable sheath 32, a stop 34, an exterior balloon catheter 36, and an interior balloon catheter 38. Also included is a deployment tube 62 disposed concentrically between the stop 34 and the exterior balloon catheter 36. A deployment balloon 64 is attached at a proximal end to the stop 34 and at distal end to the deployment tube 62.

The retractable sheath 32 is sliding disposed around the stop 34. The stop 34 has an outer diameter that is slightly smaller than an interior diameter of the retractable sheath 32, thereby allowing the two components to slide relative to each other. The stop 34 is shorter than the overall length of the device 30, allowing room distal of the stop 34 for the structure 10 and the deployment balloon 64. The retractable sheath 32 functions to protect the expandable structure 10 and the soft tissue of the patient during insertion of the device 60. The stop 34 functions to act against the expandable structure 10 to prevent the structure 10 from retracting with the sheath 32. The stop 34 is also sealed to the proximal end of the deployment balloon 64.

The stop 34 includes a lumen 42 that contains the exterior and interior balloon catheters 36 and 38, as well as the deployment tube 62. The deployment tube 62 is small enough to leave a fluid gap 66 between the stop 34 and the deployment tube 62. The deployment tube 62 is longer than the stop 34 and has sealed to it the distal end of the deployment balloon 64. The fluid gap 66 is in fluid communication with the interior of the balloon 64 and is used to inflate and deflate the balloon 64. The deployment tube 62 includes a lumen that houses the exterior balloon catheter 36 and the interior balloon catheter 38.

The interior balloon catheter 38 fits within a lumen of the exterior balloon catheter 36. The interior balloon catheter 38 is longer than the exterior balloon catheter 36 and extends distally farther than any of the other aforementioned elongate tubes 32, 34, 36, and 62. Around a distal end of the interior balloon catheter 38 there is disposed an atraumatic tip 44. The additional length of the interior balloon catheter 38 provides adequate support for the soft atraumatic tip 44.

Proximal of the atraumatic tip 44, a distal end of a tapered balloon 46 is attached to the exterior surface of the interior balloon catheter 38. A proximal end of the tapered balloon 46 is attached to the distal end of the exterior balloon catheter 36. A significant difference in the interior diameter of the exterior balloon catheter 36 and the outer diameter of the interior balloon catheter 38 creates a gap 48 therebetween. The gap 48 is in fluid communication with the interior of the tapered balloon 46 and is thus used to send a bio-compatible fluid, such as saline, to and from the tapered balloon 46 for purposes of inflating and deflating the balloon 46, respectively. Also, the interior balloon catheter 38 optionally includes a lumen through which a guidewire 50 is slidingly disposed.

In operation, the guidewire 50 may be used in conjunction with a steerable catheter (not shown) to place a distal end of the guide wire past the desired target location where the structure 10 is to be placed, such as in the pulmonary vein. Once in place, the steerable catheter is retracted off of the guidewire 50, leaving the guidewire 50 in place. The guidewire 50 is then used to locate the delivery device 30 at the desired location.

The distal end 52 of the interior balloon catheter 38 is threaded over a proximal end of the guidewire 50, and the device 30 is slowly advanced down the guidewire 50 while maintaining a stationary relationship between the guidewire 50 and the patient. While the device 30 is being advanced, the atraumatic tip 44 serves to guide the device 30 into the centers of the various body lumens en route to the desired destination as well as preventing the device 30 from causing any soft tissue damage. Notably, the atraumatic tip 44 has a narrow distal end 54 and a wider proximal end 56. Preferably, the wider proximal end 56 has a greater diameter than the diameter of the sheath 32, to prevent the relatively squared distal end of the sheath 32 from causing any damage.

Once the atraumatic tip 44 has reached the desired location where the structure 10 is to be deployed, the tip 44, as well as the interior and exterior balloon catheters 38 and 36 are advanced farther until the tapered balloon 46 extends past the distal end of the retractable sheath 32 and past the distal end of the structure 10.

Next, the balloon 46 is inflated by pumping fluid from the proximal end of the device 30, through the gap 48, and into the balloon 46. Inflating the balloon 46 not only centers the device 60 in the pulmonary vein, but it also helps anchor the device 60 at the desired location so the device 60 doesn't move axially while the structure 10 is being deployed.

Figure 6:
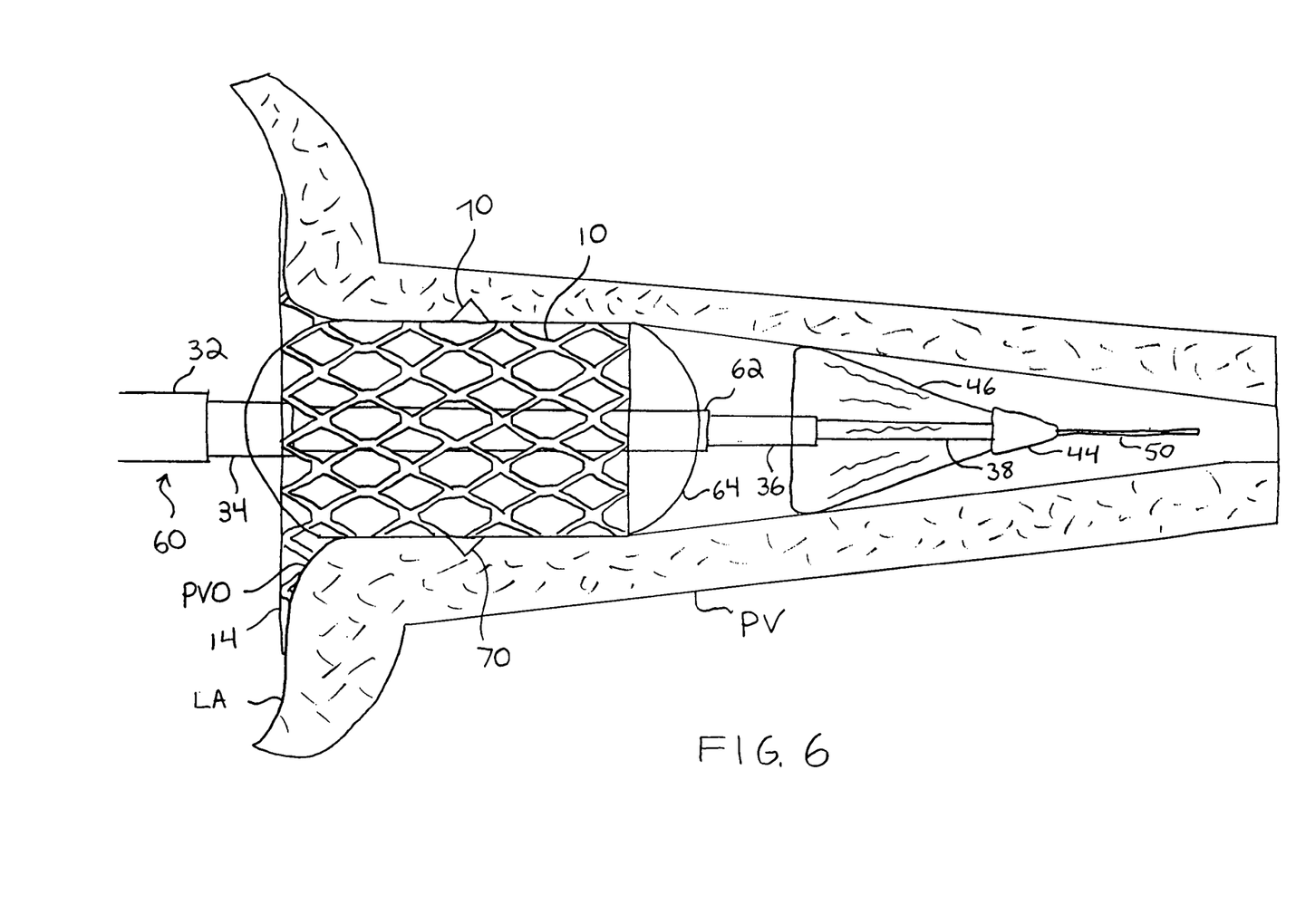

Once the balloon 46 is inflated, the sheath 32 is retracted until the expandable structure 10 is completely exposed. The structure 10, once exposed, is next deployed by pumping fluid into the gap 66 to the interior of the deployment balloon 64. The deployment balloon 64 inflates and acts against an interior surface of the structure 10, causing the structure 10 to expand. FIG. 6 shows a device 60 that has been used to deploy an expandable structure 10. A preferred shape of the tapered balloon 46 is shown. The sheath 32 has been retracted past the stop 34, and the deployment balloon 64 is fully inflated, expanding the structure 10. The structure 10 has a flared end 14 that hugs the interior wall of the left atrium LA, thereby allowing the structure 10 to completely cover the ostium of the pulmonary vein PVO.

Also shown in FIG. 6 is an incision 70 in the endothelium of the pulmonary vein that was made to inhibit the flow of electrical current between the pulmonary vein and the left atrium. The incision is being held open by the outward force of the structure 10, thereby preventing the cut conductive fibrils from reestablishing electrical communication.

The incision may be made in a variety of ways. In a preferred embodiment, a cutting balloon (not shown) is used to make the incision 70. After the steerable catheter is used to place the guidewire 50 in the desired location, the guidewire 50 is used to deliver a cutting balloon to the target site. The cutting balloon is inflated to make the incision 70 and is then deflated and removed. With the guidewire 50 still in place, a structure 10, expandable or self-expanding, is placed within the circumferential incision using the aforementioned methods.

Alternatively, the cutting balloon may be incorporated into either device 30 or 60. For example, the cutting balloon could replace the tapered balloon 46 on either device. The cutting balloon could thus be located at the desired point of incision, inflated to make the cut, deflated, and then extended distally to allow the structure 10 to be advanced under the incision 70. The structure 10 is then deployed as described above.

Although exemplary embodiments of the present invention have been described in some detail herein, the present examples and embodiments are to be considered as illustrative and not restrictive. The invention is not to be limited to the details given, but may be modified freely within the scope of the appended claims, including equivalent constructions.

What is claimed is:

1. A method of treating arterial fibrillation, comprising:
circumferentially cutting the endothelium of the pulmonary vein at a location proximate the left atrium;
delivering a prosthetic structure to the location of the cut, the structure constructed and arranged to keep the cut open, thereby preventing the endothelium from reestablishing electrical communication between the pulmonary vein and the left atrium,
wherein circumferentially cutting the endothelium of the pulmonary vein at a location proximate the left atrium comprises:
placing a cutting balloon in operable proximity to the location;
inflating the cutting balloon until a circumferential cut is effected in the endothelium of the pulmonary vein; and,
deflating the cutting balloon.

2. The method of claim 1 further comprising expanding the prosthetic structure.

3. The method of claim 1 wherein delivering a prosthetic structure to the location of the cut comprises implanting a stent at the location of the cut.

4. The method of claim 1 wherein delivering a prosthetic structure to the location of the cut comprises implanting an expandable ring at the location of the cut.

5. The method of claim 1 wherein delivering a prosthetic structure to the location of the cut comprises:
   placing a guidewire in a position to be used to guide a device to the location;
   advancing a delivery device carrying the prosthetic structure over the guidewire to the location, such that the prosthetic structure is disposed circumjacent to the incision;
   retracting a retractable sheath covering the prosthetic structure, thereby exposing the prosthetic structure to the incision; expanding the prosthetic structure.

6. The method of claim 5 wherein expanding the prosthetic structure comprises allowing the prosthetic structure to self-expand.

7. The method of claim 5 wherein expanding the prosthetic structure comprises expanding the prosthetic structure mechanically.

8. The method of claim 1, further comprising maintaining said prosthetic structure at the location of the circumferential cut at least during a period of substantial healing of the cut.

9. A device useable to deliver a prosthetic structure to the pulmonary vein of a patient for the treatment of atrial fibrillation, comprising:
   a catheter assembly having an atraumatic tip;
   a balloon, operably attached to the catheter assembly for inflation and deflation thereby; and,
   a prosthetic structure, releasably attached to the catheter assembly, whereby said prosthetic structure can be released from the catheter assembly to be maintained in the pulmonary vein when the catheter assembly is withdrawn,
   wherein the balloon comprises a cutting balloon, useable to make a circumferential incision in the pulmonary vein to inhibit the flow of electrical current between the pulmonary vein and the left atrium.

10. The device of claim 9 wherein the balloon comprises a tapered balloon useable to assist in locating the catheter assembly in the pulmonary vein when inflated.

11. The device of claim 9 further comprising a deployment balloon, operably attached to the catheter assembly and disposed within the prosthetic structure and useable to expand the prosthetic structure.

12. The device of claim 9 further comprising a retractable sheath, slidingly disposed over the prosthetic structure.

13. The device of claim 12 wherein the prosthetic structure is self-expanding such that, when the retractable sheath is retracted, the prosthetic structure expands, attaching itself to the pulmonary vein.

14. The device of claim 9 further including a central lumen for accepting a guidewire therethrough.

* * * * *